United States Patent
Lepsch et al.

(10) Patent No.: US 8,359,168 B2
(45) Date of Patent: Jan. 22, 2013

(54) FUEL IDENTIFICATION SYSTEM AND METHOD

(75) Inventors: Fernando Lepsch, Campinas (BR); Marcos Melo Araujo, Campinas (BR); Hilton Rafael Spiler, Valinhos (BR); Carlos Henrique De Oliveira Melo, Campinas (BR); Hans Hugo Eichel, Jr., Campinas (BR)

(73) Assignee: Robert Bosch Limitada, Campinas, SP (BR)

( * ) Notice: Subject to any disclaimer, the term of this patent is extended or adjusted under 35 U.S.C. 154(b) by 304 days.

(21) Appl. No.: 12/668,249

(22) PCT Filed: Jul. 14, 2008

(86) PCT No.: PCT/BR2008/000202
§ 371 (c)(1),
(2), (4) Date: Apr. 15, 2010

(87) PCT Pub. No.: WO2009/009848
PCT Pub. Date: Jan. 22, 2009

(65) Prior Publication Data
US 2010/0204928 A1 Aug. 12, 2010

(30) Foreign Application Priority Data
Jul. 13, 2007 (BR) ..................................... 0701674

(51) Int. Cl.
*G01N 33/22* (2006.01)
(52) U.S. Cl. ........ 702/27; 702/30; 702/133; 123/198 D; 123/25 C; 123/25 J; 123/549; 123/697; 73/592
(58) Field of Classification Search .................... 702/27, 702/30, 133; 123/198 C, 25 C, 25 J, 549, 123/697, 198 D; 73/592
See application file for complete search history.

(56) References Cited

U.S. PATENT DOCUMENTS
4,993,386 A * 2/1991 Ozasa et al. .................. 123/25 J
(Continued)

FOREIGN PATENT DOCUMENTS
EP 1 548 432 6/2005
(Continued)

OTHER PUBLICATIONS
Search Report and Written Opinion for PCT/BR/2008/000202 dated Dec. 10, 2008.
(Continued)

*Primary Examiner* — Carol Tsai
(74) *Attorney, Agent, or Firm* — Alston & Bird LLP

(57) ABSTRACT

The present invention relates to a fuel identification system and method normally applied to internal combustion engine vehicles of the flex-fuel type by means of which it is possible to identify the composition of the fuel used at each point in time, particularly the ratio used in a gasoline/ethanol blend or detect the presence of air or fuel in the vapor state in the fuel line, using the same device that heats the fuel. The system according to the invention comprises a heating resistor (3) having a variable resistance value as a function of its temperature, said resistor being arranged in contact with the fuel (2); a current measuring device (6), which measures the current through the variable resistor (3); and an electronic control unit (4) connected to the resistor (3) and connected to the current measuring device (6), receiving from it the measured resistor (3) current values, the electronic control unit (4) comprising data processing means to help identify fuel (2) properties based on the current in resistor (3).

12 Claims, 3 Drawing Sheets

U.S. PATENT DOCUMENTS

| | | | |
|---|---|---|---|
| 5,179,926 A | | 1/1993 | Ament |
| 5,701,863 A | * | 12/1997 | Cemenska et al. ........ 123/198 D |
| 5,912,934 A | * | 6/1999 | Acks et al. .................... 376/248 |
| 6,343,571 B1 | * | 2/2002 | Rockwell et al. ........... 123/25 C |
| 7,017,567 B2 | * | 3/2006 | Hosoya et al. ................ 123/697 |
| 7,220,386 B2 | * | 5/2007 | Ament et al. .............. 422/82.02 |
| 7,237,539 B2 | * | 7/2007 | Mello et al. ................... 123/549 |
| 7,406,871 B2 | * | 8/2008 | Sugiura ............................ 73/592 |
| 2004/0180447 A1 | * | 9/2004 | Ament et al. ................. 436/137 |
| 2005/0126551 A1 | * | 6/2005 | Mello et al. ................... 123/549 |
| 2006/0187999 A1 | * | 8/2006 | Kawanishi et al. ............. 374/43 |

FOREIGN PATENT DOCUMENTS

| | | |
|---|---|---|
| GB | 2 268 288 | 1/1994 |
| JP | 01 016957 | 1/1989 |
| JP | 01016957 A * | 1/1989 |

OTHER PUBLICATIONS

Intl. Preliminary Report on Patentability for PCT/BR2008/000202 dated Oct. 19, 2009.

* cited by examiner

FUEL IDENTIFICATION SYSTEM AND METHOD

The present invention relates to a fuel identification system and method normally applied to internal combustion engine vehicles of the flex-fuel type by means of which it is possible to identify the composition of the fuel used at each point in time, particularly the ratio used in a gasoline/ethanol blend, or to obtain information as to the physical phase of the fuel or the existence of air in the fuel line.

DESCRIPTION OF THE PRIOR ART

The world trend towards the adoption of flex-fuel vehicles aiming to reduce the consumption of non-renewable fossil fuels and expanding the use of renewable fuels, such as ethanol, thus causing less environmental damage is noteworthy. In this context, it is advantageous that the vehicle be capable of identifying the composition of the fuel that is being used at the time in order to adapt its operation to the characteristics of that fuel composition.

The prior art describes some devices that are capable of identifying the fuel being used in the vehicle, for instance, indicating the ratio of ethanol and/or gasoline present in the fuel line.

The international patent application WO 2004/029615 relates to a system for identifying gasoline and alcohol blends and a method for identifying the type of blend that provides a quick and safe identification of the types of fuels present in several compositions. The system has a circuit, in which a voltage pulse is applied to a heater during a predetermined time, so that the gasoline to be identified is heated by the heater. A temperature sensor is arranged in the vicinity of the heater to identify the fuel temperature. The type of gasoline is identified by a differential output voltage VO corresponding to the variation between the initial temperature and the peak temperature measured by the temperature sensor. In addition, the fuel is fed between the electrodes of the alcohol-in-gas concentration sensor. This concentration is measured based on the fuel inductive capacity between the electrodes when an oscillation frequency is applied.

Document JP 1016957 discloses a device for detecting the mixing rate of different kinds of fuel. The detecting device according to the Japanese document comprises a bridge circuit arranged in the fuel supply path. The circuit contains a temperature compensating resistor, a heating resistor and a control circuit that supplies electric power to both resistors so that the heating resistor maintains an invariably constant temperature at a preset value.

Then, the current which flows through the bridge circuit varies as the fuel absorbs the heat generated by the heating resistor. As the value of the heating resistor is constant, the amount of heat absorbed by the fuel varies proportionally to the current applied to the resistor. A calculation operator calculates the amount of heat absorbed by the fuel from the heating resistor according to the formula that calculates the power dissipated by the resistor ($P=R \times I^2$), which is directly dependent on the magnitude of the electric current supplied to the heating resistor by the control circuit. The calculated heat amount is applied to a formula that further considers the fuel thermal transfer coefficient k, the fuel specific heat at constant pressure $C_p$, the fuel temperature $T_o$, the fuel density $\rho$, the fuel flow rate V, the heated wire-wound resistor temperature T, and the heating resistor dimensions. After that, the specific fuel value is calculated $A=(\rho.C_p/k)$ by means of which the fuel mixing ratio is determined.

That is to say, the process for determining the fuel composition is essentially based on the value of the heat absorbed by the fuel, which corresponds to the power dissipated by the heating resistor and on a plurality of physical characteristics of the fuel, requiring quite complex calculations including second-order functions. This calculation does not depend on the use of a variable resistance as a function of temperature, since the resistor temperature shall be kept constant.

This circuit also presents the drawback of needing a temperature compensating resistor to work properly since it is based on the principle that the heating resistor temperature is constant to carry out the necessary calculations. Therefore, the control circuit should always control the resistor temperature so that it is kept at a constant value. In addition, the circuit depends on a calculation operator capable of performing very complicated operations, thus causing the system to be more expensive.

A further drawback of the prior-art systems lies in the use of an additional device, which is especially targeted to identify the fuel composition, to the fuel heating resistor.

Finally, the prior-art systems do not suggest that the same device used for heating the fuel could also be employed to identify the composition of the gasoline and ethanol blend, or identify whether the fuel is in liquid or vapor state or even determine the existence of air in the fuel line.

Objects of the Invention

A first object of the invention is to provide a system for identifying the properties of the fuel in the fuel line by means of the fuel heating resistor in a simple and safe circuit.

It is a further object of the invention to provide a system and a method capable of recognizing the mixing ratio of the fuel in the fuel line with the help of a variable resistance to heat the fuel, without the use of a compensating mechanism and temperature control for a variable resistance at constant temperature.

Another object of the invention is to provide a system that is capable of identifying when the fuel has passed from the liquid phase to the gaseous/vapor phase, and also which is the gasoline/ethanol ratio in the fuel blend, in which said system simultaneously heats the fuel.

BRIEF DESCRIPTION OF THE INVENTION

The objects of the invention are achieved by a fuel identification system comprising a heating resistor having a variable resistance value as a function of its temperature, connected to a power source that applies a voltage to the resistor, the resistor being arranged in direct contact and heat exchanging with the fuel; a current measuring device which measures the current through the variable resistor; and an electronic control unit connected to the resistor measuring the voltage applied to the resistor and connected to the current measuring device, which receives from it the measured resistor current values, and the electronic control unit comprises data processing means with the help of which it identifies fuel properties based on the resistor current.

The fuel properties identified by the electronic control unit comprise at least one of the fuel composition, the gasoline/ethanol ratio in the fuel and the physical phase of the fuel.

The electronic control unit may comprise a memory containing at least one precalculated table associating a resistor current value with a predetermined fuel composition. The precalculated table is generated by the formula:

$$U \times I = k \times A \times (T_q - T_f)$$

wherein U is the voltage applied to the resistor, I is the resistor current, k is the fuel heat transfer coefficient, A is the contact surface area with the fuel, $T_q$ is the resistor temperature and $T_f$ is the fuel temperature.

Alternatively, the system according to the invention further comprises a temperature sensor connected to the electronic control unit and arranged in contact with the fuel, wherein the sensor measures the fuel temperature and sends temperature data to the electronic control unit, and the electronic control unit identifies the fuel composition also based on the fuel temperature.

The electronic control unit may comprise a record containing the resistor temperature values associated with their respective resistance values, and has also means for controlling the voltage applied to the resistor.

The objects of the invention are also achieved by means of a fuel identification method comprising the following steps:

applying a specific voltage to a heating resistor having a variable resistance value as a function of its temperature and that is in contact and heat exchanges with the fuel;

measuring the voltage across the resistor;

measuring and monitoring the current through the resistor;

when the resistor current is in the steady state, identifying fuel properties based on the resistor current value.

The step of identifying fuel properties comprises the identification of at least one among the fuel composition, the gasoline to ethanol ratio in the fuel, and the physical phase of the fuel.

The fuel properties identification step alternatively comprises querying a precalculated table associating a resistor current value with a preset fuel composition. The precalculated table is generated by the formula:

$$U \times I = k \times A \times (T_q - T_f)$$

wherein U is the voltage applied to the resistor, I is the resistor current, k is the fuel heat transfer coefficient, A is the contact surface area with the fuel, $T_q$ is the resistor temperature and $T_f$ is the fuel temperature.

Alternatively, the step of identifying fuel properties comprises identifying that at least part of the fuel is in gaseous state when the current through the resistor decreases substantially in relation to the current corresponding to the fuel in liquid state.

The fuel identification method according to the invention can be carried out by means of a fuel identification system also according to the present invention.

BRIEF DESCRIPTION OF THE DRAWINGS

The present invention will be described below in more detail, based on an example of execution represented in the drawings.

DETAILED DESCRIPTION OF DRAWINGS

Figure 1:
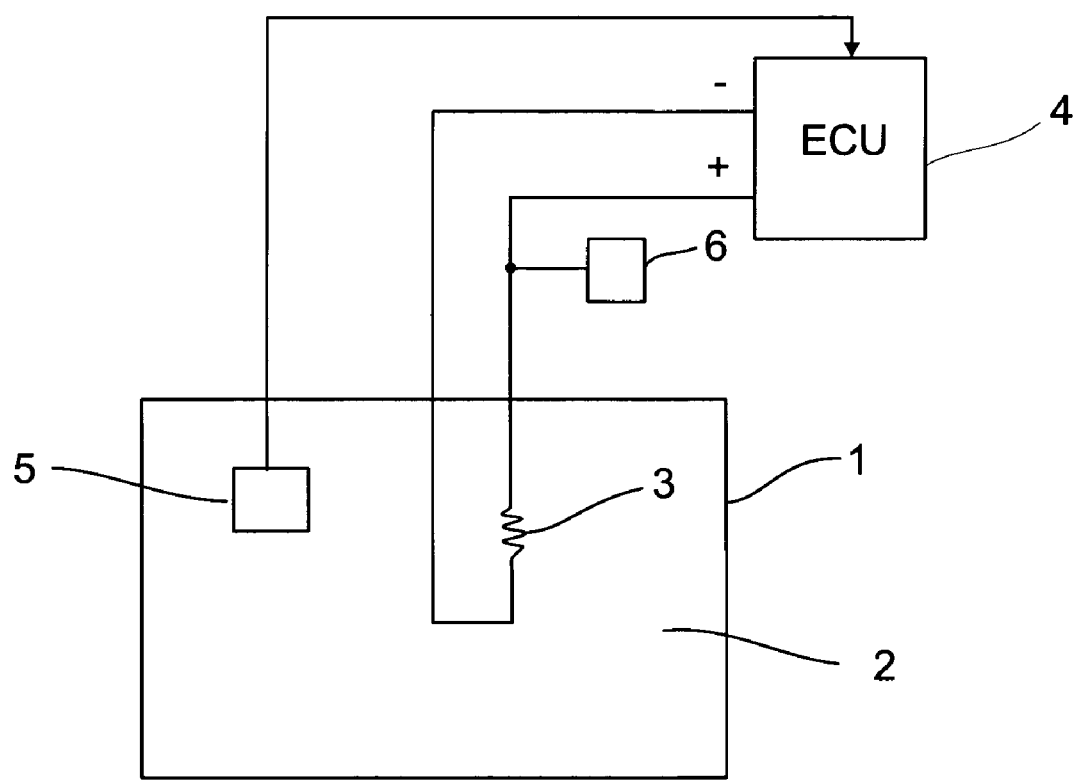
FIG. 1 depicts a schematic view of the fuel identification system according to a preferred embodiment of the invention.
Figure 2:
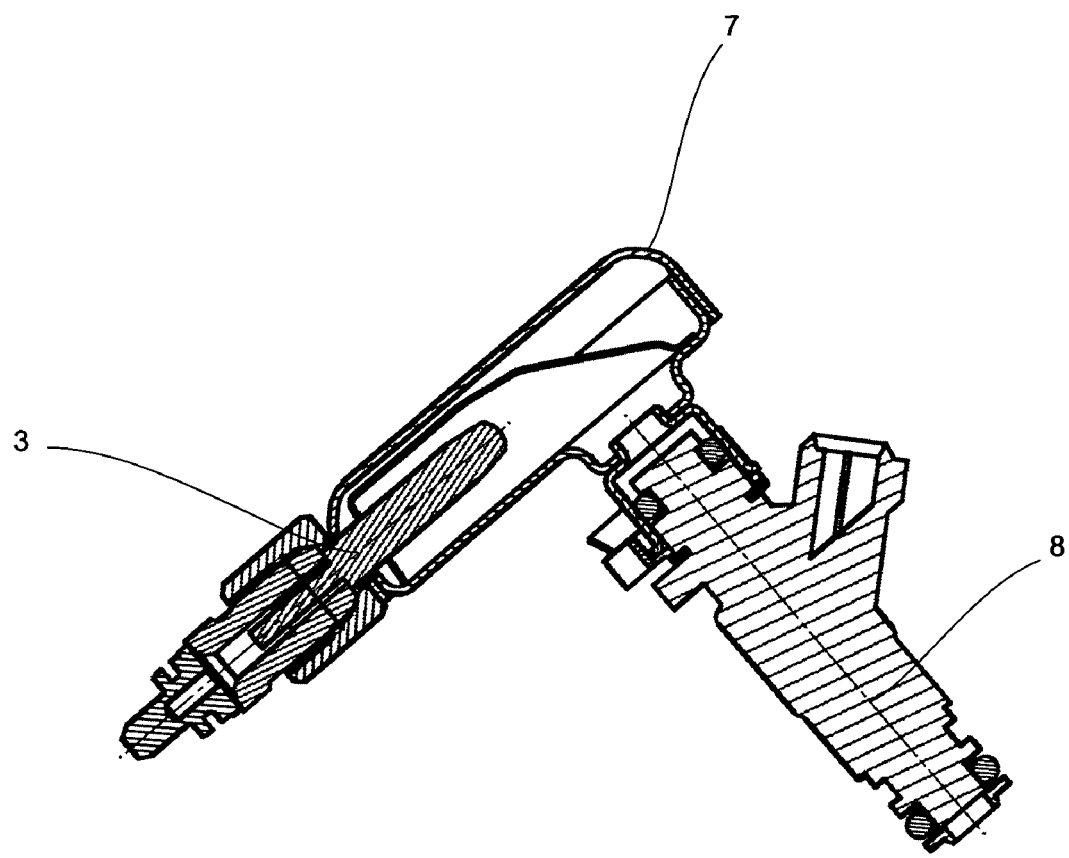
FIG. 2 shows a cross-section view of the heating resistor of the fuel identification system arranged inside the fuel gallery.

As can be seen in FIGS. 1 and 2, the fuel identification system according to the present invention comprises a variable resistor 3, whose resistance value varies as a function of its temperature. This resistor is preferably arranged, for instance, in the fuel line of an internal combustion engine vehicle, being directly in contact with the fuel 2 and is used to heat the fuel by heat transfer. The fuel line, in which resistor 3 can be arranged, consists of a fuel tank, a fuel pump, a hose, a fuel gallery 7 and at least one injector 8. The resistor 3 can be placed in any one of the integral parts of the fuel line, and, according to the present invention, preferably the resistor is housed inside the fuel gallery 7, as shown in FIG. 2.

The variable resistor 3 is connected to a power source (not illustrated) that applies a voltage to it. The resistor is also connected to an electronic control unit (ECU) 4, which measures the voltage applied to the variable resistor 3. In a preferred embodiment of the invention, the electronic control unit controls that actuating circuit which drives the variable resistor and is capable of applying different voltages to this resistor. ECU 4 further comprises a data processor capable of performing calculations as well as at least one analog-digital (A/D) converter, which converts to digital form the analog data sent to the electronic control unit, such as, for instance, the voltage values across the resistor, as well as data measured by external devices to the control unit and sent to it. In an alternative embodiment of the invention, the control unit comprises a plurality of A/D converters which work in parallel.

The ECU 4 further comprises a memory device, which can store the voltage values applied to the resistor as well as data generated by the ECU processor itself, or even other data measured by external devices and sent to the electronic control unit. The memory device also contains preprogrammed data relating to characteristics and properties from different fuel compositions. For example, the memory device may comprise at least one precalculated table associating a current, voltage and/or resistance value with a preset fuel blend composition comprising alcohol and gasoline, or else, several tables inter-relating the current and eventually the voltage across the resistor or its resistance with the physical characteristics of the fuel under specific conditions. The ECU should also contain records regarding the ratio between the temperature and the resistance of the variable resistor 3.

These tables are preferably previously generated, and the fuel compositions associated with each current and eventually voltage value in the resistor are calculated based on the heat transfer coefficient value k, corresponding to each fuel composition, and the value of the current that passes through the variable resistor when this given fuel composition is being used by the vehicle. The principles and calculations used in generating said table will be described in details later.

Figure 3:
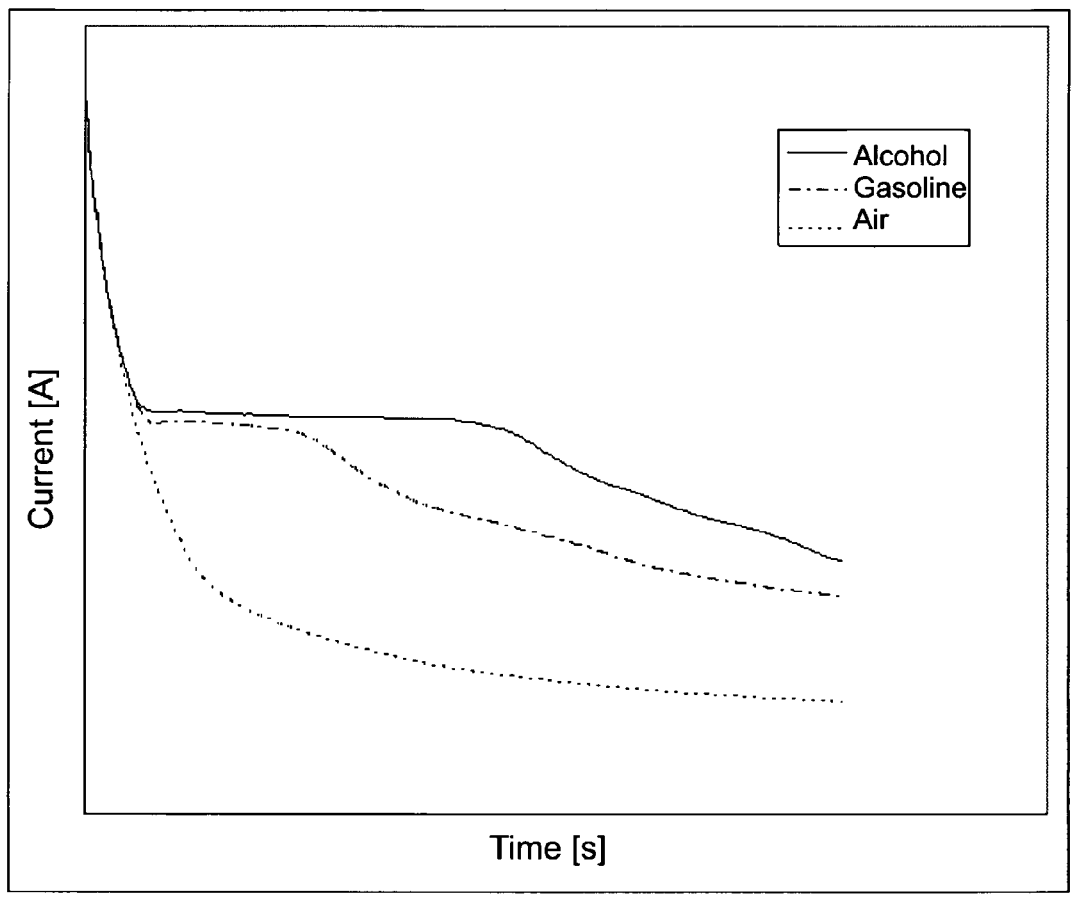
FIG. 3 depicts a graph showing the behavior of the current in the heating resistor in time, as a function of the fuel that is being heated.

For illustrative purposes only and to help understand the invention, FIG. 3 shows the current behavior through a variable resistor 3 in time when said resistor is used to heat gasoline, alcohol or air. In the beginning of the measurement operation, alcohol (solid line) and gasoline (dashed and dotted line) are in liquid state. During heating, the fuel temperature increases until the complete evaporation of the fuel. It is possible to notice in the graph that the current does not vary substantially when the fuel is in the liquid phase, or when it is changing phases (from liquid to gaseous). However, when evaporation is complete, and there is only vapor in the fuel line, the heater current decreases, because the resistor temperature increases, since the heat transfer coefficient changes significantly when a gaseous substance is heated.

The system according to the invention also detects if the fuel line is empty, i.e., filled with air. This detection is possible, since when the resistor heats the air (dotted line), the electric current also stabilizes at a lower value than the current value in the steady state for the liquid fuel. As the decrease occurs in the beginning of the measurement operation, the system may then choose to turn off heating, since its main function is to heat the fuel.

The system according to the invention comprises a resistor 3 current measuring device 6, which is connected to the ECU 4 and sends it the current values measured through the resistor. This current measuring device 6 is preferably connected in series with the variable resistor 3 and the power source, being also connected to the ECU. The current measuring device can alternatively be built in an integrated manner with the ECU itself.

The system according to the invention can alternatively have a temperature sensor 5 which is also placed on the fuel line so as to measure the fuel temperature. The temperature sensor 5 is connected to an ECU input and then sends the fuel temperature values measured to said ECU. This component is not essential for the operation of the present invention.

The system according to the invention does not require the use of the fuel temperature sensor 5, because it only needs to know the variable resistor current and the resistor voltage U in order to calculate the fuel composition or know its physical state. Based on the resistor current I and on the resistor voltage 3, the ECU can also determine what is the value of the resistance and the resistor temperature $T_q$.

If it is desired that the system according to the invention obtains the initial fuel temperature values, then the system can use the temperature data from the water temperature sensor or the air temperature sensor, which are normally used in automotive vehicles. To this end, these sensors should send data directly or indirectly to ECU 4. The initial fuel temperature will be equal to the air or water temperature. Thus, there is no need to implement an additional fuel temperature sensor inside the fuel line.

In addition, the system according to the invention alternatively has a timer (not illustrated), which is preferably integrated directly to the ECU 4. This timer will determine the time interval needed for the resistor 3 current to stabilize and reach steady state.

The fuel identification system and method according to the invention are essentially based on the fuel properties determination principle based on the value of the current through the variable resistor. Therefore, this variable resistor works as a sensor of the fuel characteristics and physical properties, as well as a fuel heater, because the heat dissipated by said resistor will heat the fuel until it reaches the evaporation temperature. Therefore, there is no need to use two physical components to carry out these two different functions, because the fuel heating and the fuel composition determination functions are performed by a same component.

The system and method according to the invention can also identify which is the fuel composition, for instance, the ethanol/gasoline ratio in the blend, obtain information about the physical phase of fuel inside the fuel line or determine whether the line is empty or not. Although the preferred embodiments of the invention described below are directed to these two particular uses, the scope of the present invention is not limited to said uses.

The preferred embodiments of the system and method according to the invention will be described in detail below.

Initially, ECU 4 controls a power source which applies a specific voltage to resistor 3, which is arranged in the fuel line 1. This voltage is measured by ECU 4. As this voltage is applied, an electric current is passed through the variable resistor 3, increasing its temperature. Thus, the resistor begins to dissipate the heat that is absorbed by fuel 2 around it, heating it. However, this fuel heat dissipation directly depends on the fuel heat transfer coefficient k, which varies as a function of the fuel composition as well as its physical phase. For instance, the heat transfer coefficient of a specific fuel composition in gaseous state is higher than the heat transfer coefficient of the same fuel composition in liquid state. It is important to note that the heat transfer coefficient assumes a different specific value for each fuel blend ratio, or desired fuel composition.

In the beginning of the resistor 3 and fuel heating, there is a transient phase in which the power dissipated by the resistor is variable in time. The variable heat dissipation causes variation in the resistor temperature, which then causes variation in the value of its resistance. The variation of the resistance value causes variation in the current through resistor 3, which, in turn, causes variation in the heat dissipated by the resistor, causing variation again in the resistor temperature. This successive variation cycle of the resistor resistance, current and temperature values is repeated until the system stabilizes and reaches the steady state.

The resistor current values are measured by the current meter 6, and are stored and monitored in time by ECU 4. The voltage values U are also measured by ECU and can be stored in it. In a preferred embodiment of the invention, the time interval between the moment in which voltage is applied to the resistor and the moment the system reaches steady state is calculated by the timer and this value is stored in the ECU memory, and can later be used for calculating some of the properties of the fuel composition.

The current through the resistor 3 is measured by the current measuring device 6 and monitored by ECU also during the transient phase to enable the identification of the start of the system operation in the steady state, when the value of the current stabilizes.

Alternatively, the fuel temperature data $T_f$ measured by the temperature sensor 5 or any other automotive vehicle sensor in the transient phase is sent to ECU, and can be stored in it. This step is not essential to the implementation of the invention.

When the resistance R, current I and temperature $T_q$ values of resistor 3 reach steady state and stabilize, the fuel properties identification step is carried out. The resistor temperature is designated by $T_q$, because it is the hottest temperature in the system. The fuel 2 is always at a cooler temperature $T_f$ than that of the resistor 3.

Based on the value of the resistor current I measured by the current measuring device 5, and also on the voltage across the resistor, ECU 4 identifies with the aid of its data processing means some of the fuel properties, such as the fuel composition, for instance, the ethanol/gasoline ratio or the physical phase of the fuel inside the fuel line. In a preferred embodiment of the invention, having the values of the current I and the voltage U, ECU 4 queries at least one precalculated table registered in its memory device associating each current value I and eventually voltage value U with a preset fuel composition and thus determines the fuel composition that is being used at the time.

The table that associates each current value I with a preset fuel composition is generated based on formula (I) below:

$$U \times I = k \times A \times (T_q - T_f)$$

wherein U is the voltage across the variable resistor, I is the resistor current, k is the fuel heat transfer coefficient, A is the contact surface area with the fuel, $T_q$ is the resistor temperature and $T_f$ is the fuel temperature.

The voltage U across the resistor is also always measured by the electronic control unit, because the current through the resistor also depends on the voltage.

In the steady state, the current values I, the resistor temperature $T_q$ and the fuel temperature $T_f$ remain stable. The value of A is known by the system and is constant during system operation. Given that R is a variable resistor whose resistance and thus current vary as a function of its temperature, then measuring the current and the voltage on the resistor is enough to determine the values of the resistor resistance and temperature $T_q$. With regard to the fuel temperature $T_f$ to start the system operation, measuring the initial fuel temperature is enough; this temperature will be equal to the initial resistor temperature $T_q$ and to the room temperature.

Applying the value of all these variables to the formula in question, the k value is obtained. As the fuel heat transfer coefficient k is specific for each fuel composition, then by knowing this value, it is possible to know the composition of the fuel blend in the fuel line.

However, these calculations are not necessarily performed by the system, because the system already has precalculated tables directly associating the current values I and eventually the voltage values and the fuel composition in each possible case.

The system and the method according to the invention can further be used to detect whether the fuel in the fuel line is in liquid or vapor state. When the fuel is in vapor state, is heat transfer coefficient k is much higher than that of the fuel in liquid state. Thus, when the fuel starts to transform into vapor, the resistor temperature varies quickly and the resistor resistance and the current through the resistor also start to vary at a very quick rate.

Before fuel evaporation, the system is operating in the steady state, and the current through the resistor is stabilized at a known value, depending on the voltage across the resistor 3. When fuel evaporation starts, the resistor current 3 rapidly starts to decrease. The system then detects that the current is decreasing and moving away from the value of the current in the steady state. When this current variation becomes more significant, for instance, with a current value around 50%, or slightly higher, in the steady state for the liquid fuel, then the system identifies that at least one part of the fuel is in liquid state, even before the current is stabilized at a fixed value corresponding to the steady state of the gaseous fuel. Therefore, the system and method according to the invention are capable of detecting whether the fuel is in liquid state or at least partially in vapor state by means of the behavior of the current value in resistor 3.

The use of a fuel temperature sensor 5 is not essential to the operation of the system and method according to the present invention. Mainly in the case of applying the system and method according to the invention merely for detecting the physical phase of the fuel, the use of the temperature sensor is not required, because the desired results enable a higher error margin and can be obtained by means of less precise values. However, the temperature sensor enables the heat transfer coefficient calculations to be carried out in a more precise manner, obtaining more accurate results.

The system and method according to the invention are clearly different from the prior-art ones because they enable the identification of the fuel blend ratio to be carried out merely by a variable resistor 3, which is also used to heat the fuel. Therefore, a same device simultaneously carries out two different functions, which, in the current state of the art, are performed by two separate devices. Thus, the system according to the invention does not require the use of auxiliary devices, such as the Wheatstone bridge, to measure the fuel blend composition in addition to the heating resistor.

Furthermore, the calculation effected by the system according to the invention is based on principles different from the prior-art ones. The system and method of the present invention only use the value of the current and voltage applied to the variable resistor to directly calculate the alcohol/gasoline ratio in the fuel blend, without the need to perform complex mathematical operations. The invention enables the resistor temperature to vary in time during the entire fuel heat transfer coefficient measurement, both during the transient phase and during the steady state operation. After all, the use of a resistor with variable resistance as a function of its temperature and the variation of the resistor temperature, resistance and current values are precisely the characteristics that enable the system operation as proposed and the execution of the method according to the invention.

Actually, the calculation of the heat transfer coefficient basically depends on the voltage and current related to the temperature of the variable resistor, which is the hottest body in the system. Whereas in the prior-art device described in document JP 1016957, the heat transfer coefficient calculation directly depends on the temperature of the fuel, which is the coldest body in the system.

The system and method according to the present invention enable the calculation of the heat transfer coefficient value and the consequent determination of the fuel composition by means of queries to the tables stored in the system. This promotes efficiency in the system and does not require the use of processors capable of performing very complex operations.

The system and method according to the invention can also be used to determine the composition of other blends and fuels other than ethanol and gasoline. To this end, one should know the correlation between the heat transfer coefficient and the fuel composition associated with it, calculate the corresponding currents generated in the variable resistor based on formula (I) and program the electronic control unit according to said parameters.

Having described examples of the invention with reference to its preferred embodiments, it is to be understood that the scope of the present invention embraces other possible variations, being limited solely by the appended claims, including the possible equivalents therein.

The invention claimed is:

1. A fuel identification system, comprising:
a fuel heating resistor having a variable resistance value as a function of its temperature, connected to a power source that applies a voltage to the resistor, said resistor being in direct contact and exchanging heat with the fuel, and having its temperature varied during the fuel heating operation;
a current measuring device that measures the current through the variable resistor; and
an electronic control unit connected to the resistor, measuring the voltage applied to the resistor, and connected to the current measuring device so as to receive therefrom the values measured for the resistor current, said electronic control unit comprising data processing means with the aid of which said electronic control unit identifies fuel properties based on the resistor current and on the formula $$U \times I = k \times A \times (T_q - T_f)$$

wherein U is the voltage applied to the resistor, I is the resistor current, k is the fuel heat transfer coefficient, A is the contact surface area with the fuel, $T_q$ is the resistor temperature and $T_f$ is the fuel temperature.

2. A fuel identification system according to claim 1, wherein the fuel properties identified by the electronic control unit comprise at least one among the fuel composition, the gasoline/ethanol ratio in the fuel, the physical phase of the fuel and the presence of air in the line.

3. A fuel identification system according to claim 1, wherein the electronic control unit comprises a memory containing at least one precalculated table associating a resistor current value with a preset fuel composition.

4. A fuel identification system according to claim 1, further comprising a temperature sensor connected to the electronic control unit and arranged in contact with the fuel, wherein the sensor measures the fuel temperature and sends the temperature data to the electronic control unit, and the electronic control unit identifies the fuel composition also based on the fuel temperature.

5. A fuel identification system according to claim 1, wherein the electronic control unit comprises a record containing the resistor temperature values associated with their respective resistance values.

6. A fuel identification system according to claim 1, wherein the electronic control unit comprises means of controlling the voltage applied to the resistor.

7. A fuel identification method comprising the steps of:
applying a determined voltage to a heating resistor having a variable resistance value as a function of its temperature and that is in contact and exchanges heat with the fuel, wherein the temperature of the heating resistor varies during the fuel heating;
measuring the voltage across the resistor;
measuring and monitoring the current through the resistor;
when the resistor current is in the steady state, identifying fuel properties based on the resistor current value and on the formula:

$$U \times I = k \times A \times (T_q - T_f)$$

wherein U is the voltage applied to the resistor, I is the resistor current, k is the fuel heat transfer coefficient, A is the contact surface area with the fuel, $T_q$ is the resistor temperature and $T_f$ is the fuel temperature.

8. A fuel identification method according to claim 7, wherein the fuel properties identification step comprises identifying at least one among the fuel composition, the gasoline to ethanol ratio in the fuel, the physical phase of the fuel and the presence of air in the line.

9. A fuel identification method according to claim 7, wherein the fuel properties identification step comprises querying a precalculated table associating a resistor current value with a preset fuel composition.

10. A fuel identification method according to claim 7, wherein the step of identifying fuel properties comprises identifying that at least part of the fuel is in gaseous state when the current through the resistor decreases substantially in relation to the current in the steady state corresponding to the fuel in liquid state.

11. A fuel identification method according to claim 7, wherein the step of identifying the fuel properties comprises identifying if the fuel line is empty, thus turning off heating.

12. The fuel identification method according to claim 7, wherein the method is carried out by means of a fuel identification system comprising:
a fuel heating resistor having a variable resistance value as a function of its temperature, connected to a power source that applies a voltage to the resistor, said resistor being in direct contact and exchanging heat with the fuel, and having its temperature varied during the fuel heating operation;
a current measuring device that measures the current through the variable resistor; and
an electronic control unit connected to the resistor, measuring the voltage applied to the resistor, and connected to the current measuring device so as to receive therefrom the values measured for the resistor current, said electronic control unit comprising data processing means with the aid of which said electronic control unit identifies fuel properties based on the resistor current and on the formula $$U \times I = k \times A \times (T_q - T_f)$$

wherein U is the voltage applied to the resistor, I is the resistor current, k is the fuel heat transfer coefficient, A is the contact surface area with the fuel, $T_q$ is the resistor temperature and $T_f$ is the fuel temperature.

* * * * *

UNITED STATES PATENT AND TRADEMARK OFFICE
CERTIFICATE OF CORRECTION

PATENT NO. : 8,359,168 B2  Page 1 of 1
APPLICATION NO. : 12/668249
DATED : January 22, 2013
INVENTOR(S) : Lepsch et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 398 days.

Signed and Sealed this
First Day of September, 2015

Michelle K. Lee
*Director of the United States Patent and Trademark Office*